United States Patent
Moszner et al.

(10) Patent No.: US 11,357,709 B2
(45) Date of Patent: Jun. 14, 2022

(54) DENTAL MATERIALS BASED ON REDOX SYSTEMS WITH LOW-ODOUR CUMENE HYDROPEROXIDE DERIVATIVES

(71) Applicant: Ivoclar Vivadent AG, Schaan (LI)

(72) Inventors: Norbert Moszner, Triesen (LI); Thomas Köhler, Reichenau (DE); Johannes Schädlich, St. Margareten (CH); Jörg Angermann, Sargans (CH)

(73) Assignee: Ivoclar Vivadent AG, Schaan (LI)

( * ) Notice: Subject to any disclaimer, the term of this patent is extended or adjusted under 35 U.S.C. 154(b) by 317 days.

(21) Appl. No.: 16/778,034

(22) Filed: Jan. 31, 2020

(65) Prior Publication Data
US 2020/0253837 A1    Aug. 13, 2020

(30) Foreign Application Priority Data

Feb. 7, 2019   (EP) ..................... 19156084

(51) Int. Cl.
*A61K 6/887* (2020.01)
*A61K 6/71* (2020.01)

(52) U.S. Cl.
CPC ............... *A61K 6/887* (2020.01); *A61K 6/71* (2020.01)

(58) Field of Classification Search
None
See application file for complete search history.

(56) References Cited

U.S. PATENT DOCUMENTS

| | | | | |
|---|---|---|---|---|
| 3,009,963 A | * | 11/1961 | Hock | C07C 29/132 568/311 |
| 3,796,757 A | * | 3/1974 | Chang | C07C 409/38 526/208 |
| 3,991,008 A | | 11/1976 | Temin et al. | |
| 4,582,823 A | | 4/1986 | Heffner et al. | |
| 7,275,932 B2 | | 10/2007 | Jin | |
| 7,498,367 B2 | | 3/2009 | Qian | |
| 8,247,470 B2 | | 8/2012 | Yarimizu et al. | |
| 2003/0134933 A1 | * | 7/2003 | Jin | A61K 6/54 523/120 |
| 2007/0040151 A1 | * | 2/2007 | Utterodt | A61K 6/887 252/182.13 |
| 2007/0100019 A1 | | 5/2007 | Sun | |
| 2008/0003542 A1 | * | 1/2008 | Jin | A61K 6/54 523/118 |
| 2010/0240797 A1 | * | 9/2010 | Yarimizu | C09D 4/00 523/118 |
| 2010/0249266 A1 | * | 9/2010 | Yarimizu | A61K 6/887 523/116 |
| 2010/0311864 A1 | | 12/2010 | Arita et al. | |
| 2012/0059083 A1 | * | 3/2012 | Tokui | A61K 6/30 526/147 |
| 2014/0094578 A1 | * | 4/2014 | Tanaka | C08K 5/37 526/214 |
| 2017/0014311 A1 | * | 1/2017 | Ishizuka | A61K 6/887 |
| 2017/0128328 A1 | * | 5/2017 | Moszner | A61K 6/20 |
| 2018/0265527 A1 | * | 9/2018 | Moszner | C08F 222/1025 |
| 2019/0008730 A1 | * | 1/2019 | Fujimi | A61K 6/62 |
| 2020/0253837 A1 | * | 8/2020 | Moszner | A61K 6/17 |

OTHER PUBLICATIONS

Innovation Q plus PG pub search (Year: 2022).*
Google Scholar search (Year: 2022).*
STIC Structure search (Year: 2021).*

* cited by examiner

*Primary Examiner* — Peter A Salamon
(74) *Attorney, Agent, or Firm* — Ann M. Knab; Thad McMurray

(57) ABSTRACT

Radically polymerizable dental material, which contains a combination of a thiourea derivative and a hydroperoxide according to the following Formula (I) as initiator system for the radical polymerization:

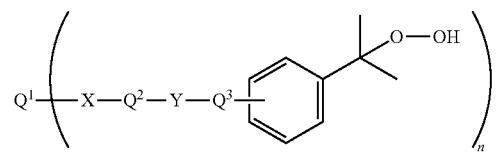

Formula I

24 Claims, No Drawings

DENTAL MATERIALS BASED ON REDOX SYSTEMS WITH LOW-ODOUR CUMENE HYDROPEROXIDE DERIVATIVES

CROSS-REFERENCE TO RELATED APPLICATIONS

This application claims priority to European patent application No. 19156084.6 filed on Feb. 7, 2019, the disclosure of which is incorporated herein by reference in its entirety.

FIELD OF INVENTION

The present invention relates to radically polymerizable compositions with a cumene hydroperoxide redox initiator system which contains low-odour cumene hydroperoxide derivatives. The compositions are particularly suitable as dental materials, for example as prosthesis materials, cements, adhesives and composites for direct fillings.

BACKGROUND

The main areas of use of polymers in the dental field are removable prosthetics (e.g. teeth and prosthesis base materials) and fixed prosthetics (e.g. veneering materials, crowns or cements), filling materials (e.g. direct or indirect filling composites, fixing cements or adhesives) or auxiliary materials (e.g. impression materials). The polymers are usually obtained by radical polymerization of suitable compositions which contain a polymerizable organic matrix, usually a mixture of monomers, initiator components and stabilizers.

Methyl methacrylate (MMA) (prosthesis materials), mixtures of functionalized monomers, such as e.g. 2-hydroxyethyl methacrylate (HEMA), or acid-group-containing adhesive monomers, such as e.g. 10-methacryloyloxydecyl dihydrogen phosphate (MDP), with dimethacrylates (adhesives) or mixtures which contain exclusively dimethacrylates (composite cements and filling composites) are usually used as monomers. Dimethacrylates often used are 2,2-bis[4-(2-hydroxy-3-methacryloyloxypropyl)phenyl]propane (bis-GMA) and 1,6-bis-[2-methacryloyloxyethoxycarbonylamino]-2,2,4-trimethylhexane (UDMA), which have a high viscosity and result in polymerizates with very good mechanical properties. Above all, triethylene glycol dimethacrylate (TEGDMA), 1,10-decanediol dimethacrylate ($D_3MA$) or bis(3-methacryloyloxymethyl)tricyclo-[5.2.1.02.6]decane (DCP) are used as reactive diluents.

Methacrylate-based dental materials are cured by radical polymerization, wherein radical photoinitiators (light curing, direct filling composites and adhesives), thermal initiators (indirect composites or prosthesis materials) or redox initiator systems (composite cements) are used depending on the field of use. The combination of photoinitiators with redox initiators is also known, e.g. when filling deep cavities.

Redox systems are used above all when there is the risk of incomplete curing, because of a low monomer reactivity e.g. in the case of prosthesis materials or because of insufficient irradiation in the case of fixing cements.

In order to guarantee a sufficient storage stability of the materials, materials based on redox initiators are usually used as so-called two-component systems (2C systems), wherein the oxidant (peroxide or hydroperoxide) and the reducing agent (amines, sulfinic acids, barbiturates, thiourea etc.) are incorporated into two separate components. These components are mixed with each other shortly before use. The two components must be matched such that their homogeneous blending and use is easily possible and that a processing time sufficient for dental purposes is achieved. By the processing time is meant the period of time between the blending of the two components and the start of curing of the mixed material. It should lie in a range of from approximately 90 to 150 s. On the other hand, the curing time, i.e. the period until complete hardening of the materials, must not be too long. A curing time of approx. 3 to 5 min is optimal.

For a long time, redox initiator systems which are based on a mixture of dibenzoyl peroxide (DBPO) with tertiary aromatic amines, such as e.g. N,N-diethanol-p-toluidine (DEPT), N,N-dimethyl-sym-xylidine (DMSX) or N,N-diethyl-3,5-di-tert-butylaniline (DABA) have primarily been used for dental composite cements. With DBPO/amine-based redox initiator systems the processing and curing time can be set relatively well in combination with phenolic inhibitors. A disadvantage of such DBPO/amine systems is the discolorations which are caused by a slow oxidation of the amines. Moreover, the radical formation in the case of DBPO/amine-based redox initiator systems is impaired by acids and thus also by acid monomers, which are normally used to prepare enamel-dentine adhesives. The amine component is protonated by an acid-base reaction and thereby deactivated.

The above disadvantages can be partially overcome with hydroperoxide redox initiator systems, because no tertiary amines are needed as reducing agent. Moreover, hydroperoxides are more thermally stable than peroxides. Cumene hydroperoxide has for example a 10-hour half-life temperature $T_{1/2}$ of 158° C.; the 10-hour half-life temperature $T_{1/2}$ of DBPO is only 73° C.

DE 26 35 595 C2 and corresponding U.S. Pat. No. 3,991,008, which is hereby incorporated by reference in its entirety, discloses polymerizable dental filling compounds which contain a substituted thiourea reducing agent in combination with a hydroperoxide oxidant as initiator system. The materials are said to have an improved colour stability, an excellent cure rate and an improved storage stability.

EP 1 693 046 B1 and corresponding U.S. Pat. No. 7,498,367, which is hereby incorporated by reference in its entirety, discloses dental cements and core build-up materials which contain a (2-pyridyl)-2-thiourea derivative in combination with a hydroperoxide, in which the hydroperoxide group is bonded to a tertiary carbon atom.

WO 2007/016508 and corresponding US 2007100019, which is hereby incorporated by reference in its entirety, discloses a polymerizable dental composition which contains a thiourea derivative in combination with a hydroperoxide as initiator system. The composition does not contain monomers with acid groups.

According to EP 1 754 465 B1 and corresponding U.S. Pat. No. 4,582,823, which is hereby incorporated by reference in its entirety, the reactivity of the cumene hydroperoxide/acetyl thiourea system can be increased by the addition of soluble copper compounds.

U.S. Pat. No. 7,275,932 B2, which is hereby incorporated by reference in its entirety, proposes the use of hydroperoxides and thiourea derivatives in combination with an acid compound as accelerator. Preferred acid compounds are acrylates and methacrylates with acid groups such as e.g. methacrylic acid.

EP 2 233 544 A1 and corresponding U.S. Pat. No. 8,247,470, which is hereby incorporated by reference in its entirety, and EP 2 258 336 A1 and corresponding US 20100311864, which is hereby incorporated by reference in its entirety, disclose dental materials which contain a hydroperoxide and a thiourea derivative in combination with a vanadium compound as accelerator.

Initiator systems based on hydroperoxides and in particular based on cumene hydroperoxide have become considerably important in the avoidance of the disadvantages associated with peroxide/amine systems. A disadvantage of cumene hydroperoxide is its typically aromatic odour, which is evocative of xylenes and toluene and which is above all perceived as unpleasant in the case of materials for intraoral use.

SUMMARY

The object of the invention is to provide dental materials which do not have the disadvantages of the state of the art. The materials are to be low-odour, to have a high storage stability and to display no discolorations, but at the same time to harden rapidly and still have a processing time that is suitable for dental purposes. The materials are furthermore to have good mechanical properties.

DETAILED DESCRIPTION

This object is achieved by radically polymerizable dental materials which contain a combination of a thiourea derivative and a hydroperoxide according to the following Formula (I) as initiator system for the radical polymerization,

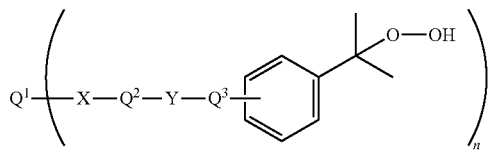

Formula I in which the variables have the following meanings:
$Q^1$ an n-valent, aromatic, aliphatic, linear or branched $C_1$-$C_{14}$ hydrocarbon radical, which can be interrupted by one or more S and/or O atoms and which can be unsubstituted or substituted by one or more substituents which are preferably selected from —OH, —OR$^1$, —Cl and —Br, wherein R$^1$ is an aliphatic, linear or branched $C_1$-$C_{10}$ hydrocarbon radical, X, Y independently of each other are in each case absent, —O—, —COO—; —CONR$^2$—, or —O—CO—NR$^3$—, wherein R$^2$ and R$^3$ independently of each other represent H or a $C_1$-$C_5$ alkyl radical, preferably H, methyl and/or ethyl, particularly preferably H, and wherein X and Y are preferably not absent at the same time, $Q^2$ is absent with, an aliphatic, linear or branched $C_1$-$C_{14}$ alkylene radical, which can be interrupted by S and/or O atoms and which can be unsubstituted or substituted by —OH, —OR$^4$, —Cl and/or —Br, wherein R$^4$ is an aliphatic, linear or branched $C_1$-$C_{10}$ hydrocarbon radical, $Q^3$ a $C_1$-$C_3$ alkylene group or is absent, preferably —CH$_2$— or is absent wherein X and/or Y is absent if $Q^2$ is absent n 1, 2, 3 or 4, and wherein the substitution on the aromatic compound takes place in position 2, 3 or 4, relative to the cumene hydroperoxide group.

Formula I extends only to those compounds which are compatible with the theory of chemical valence. The indication that a radical is interrupted e.g. by one or more O atoms is to be understood to mean that these atoms are inserted in each case into the carbon chain of the radical. These atoms are thus bordered on both sides by C atoms and cannot be terminal. $C_1$ radicals cannot be interrupted. The groups —COO—, —CONR$^2$—, and —O—CO—NR$^3$— can be arranged in any desired orientation. For example, —COO— represents both —CO—O— and —O—CO—. Corresponding to the usual nomenclature, by aromatic hydrocarbon radicals is also meant those radicals which contain aromatic and non-aromatic groups. A preferred aromatic radical is, for example, the p-isopropylphenyl radical.

The variables preferably have the following meanings:
$Q^1$ a mono- or divalent, aliphatic, linear or branched $C_1$-$C_{10}$ hydrocarbon radical, which can be interrupted by one or more O atoms, preferably one O atom, and which can be substituted by one or more, preferably one, substituents which are selected from —OH and —OR$^1$, or is preferably unsubstituted, wherein R$^1$ is an aliphatic, linear or branched $C_1$-$C_6$ hydrocarbon radical, X, Y independently of each other are in each case absent with, —O—, —COO— or —O—CO—NR$^3$—, wherein R$^3$ represents H or a $C_1$-$C_5$ alkyl radical, preferably H, methyl and/or ethyl and quite particularly preferably H, and wherein X and Y are preferably not absent at the same time, $Q^2$ is absent, a linear or branched $C_1$-$C_{10}$ alkylene radical, which can be interrupted by one or more O atoms, preferably one O atom, and which can be substituted by one or more, preferably one, substituents which are selected from —OH and —OR$^4$, or is preferably unsubstituted, wherein R$^4$ is an aliphatic, linear or branched $C_1$-$C_6$ hydrocarbon radical, n 1 or 2, and wherein the substitution on the aromatic compound takes place in position 3, preferably in position 4.

The variables particularly preferably have the following meanings:
$Q^1$ a mono- or divalent, aliphatic, linear or branched $C_1$-$C_5$ hydrocarbon radical, which can be interrupted by one O atom and which can be substituted by one OH group,

X —COO—,

Y is absent $Q^2$ is absent with or a linear $C_1$-$C_3$ alkylene radical, n 1 or 2, and wherein the substitution on the aromatic compound takes place in position 4.

The variables most preferably have the following meanings:
$Q^1$ a mono- or divalent, aliphatic, branched, preferably linear $C_1$-$C_4$ hydrocarbon radical,

X —COO—,

Y is absent $Q^2$ is absent or a methylene radical, n 1 or 2, and wherein the substitution on the aromatic compound takes place in position 4.

The preferred, particularly preferred and most preferred definitions given for the individual variables can be selected in each case independently of each other. Compounds in which all the variables have the preferred, particularly preferred and most preferred definitions are naturally particularly suitable according to the invention.

The hydroperoxides of Formula I are effective as redox initiator system in combination with a thiourea derivative. According to the invention it was surprisingly found that they do not have the unpleasant odour of cumene hydroperoxide.

Hydroperoxide derivatives of Formula I can be prepared, for example, by esterifying substituted isopropylbenzene derivatives having a terminal OH group with a suitable carboxylic acid and then converting them into hydroperoxide derivatives of Formula I according to the invention by oxidation:

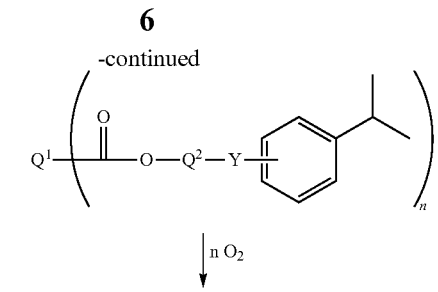

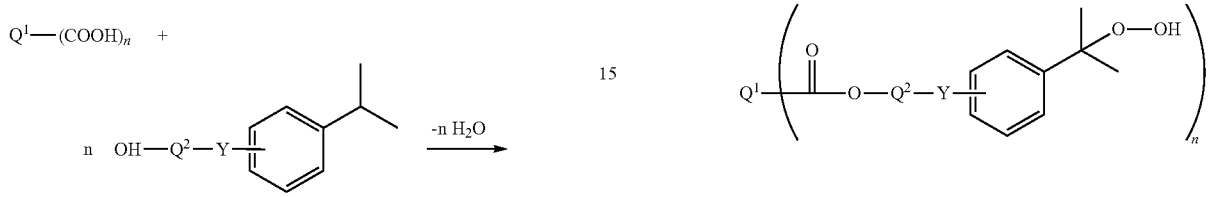

A specific example is:

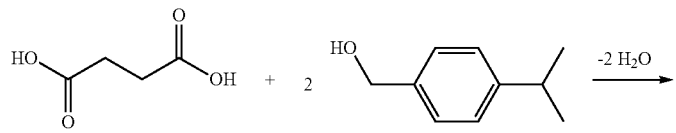

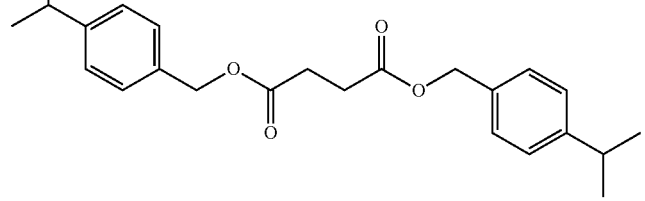

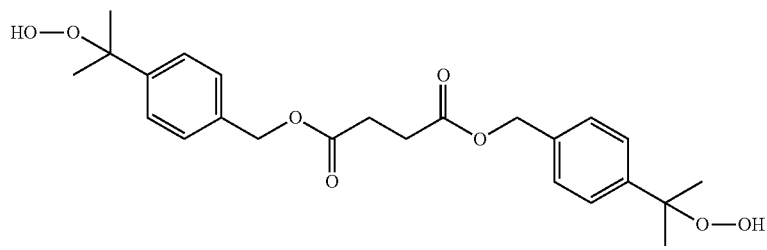

Hydroperoxide derivatives of Formula I preferred according to the invention are:

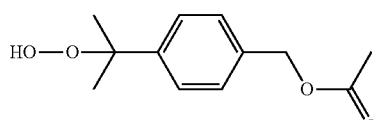 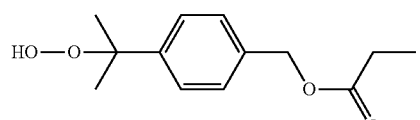

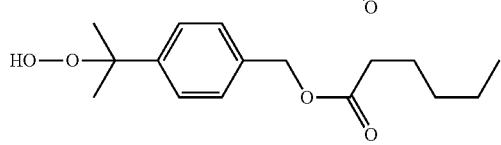 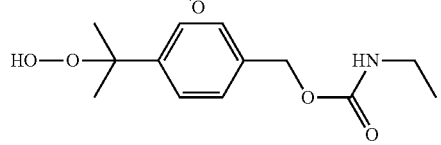

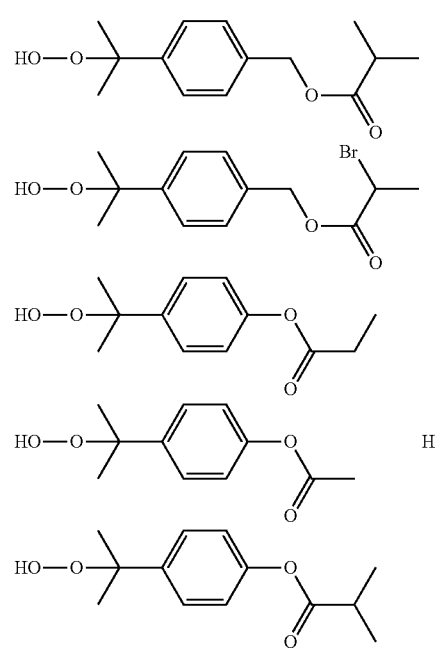
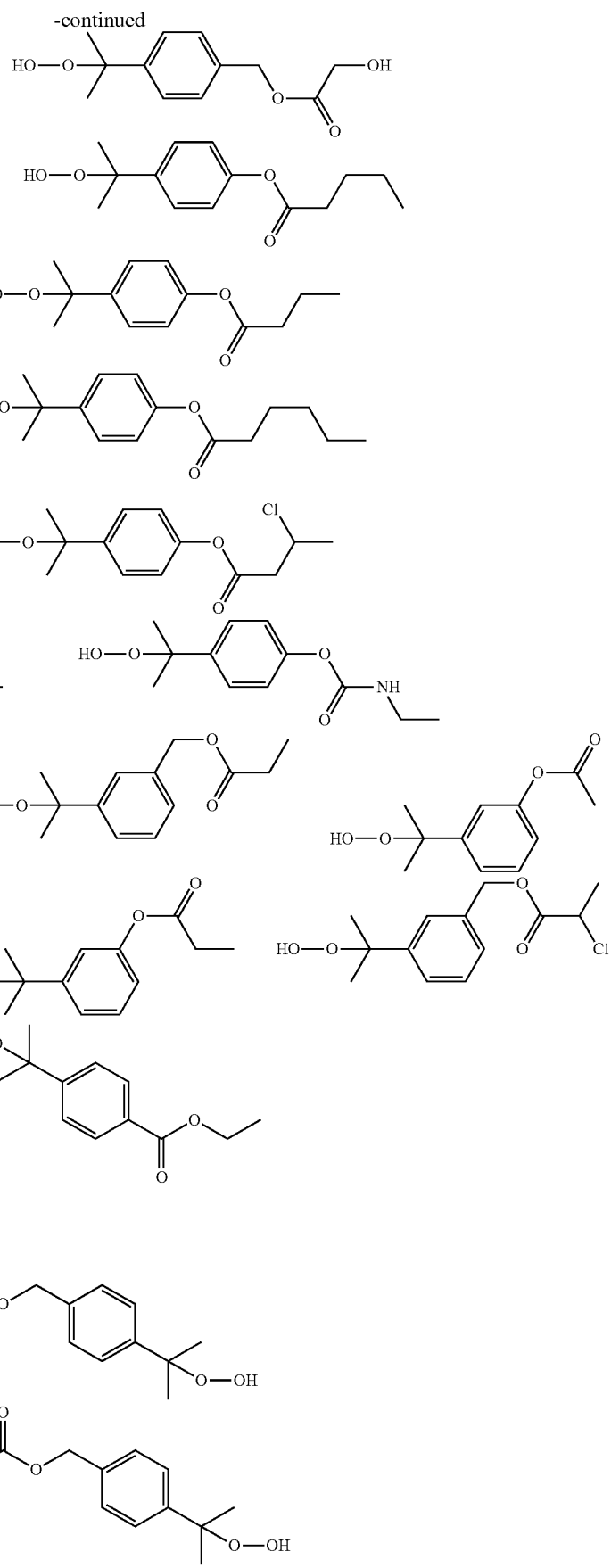
-continued

-continued
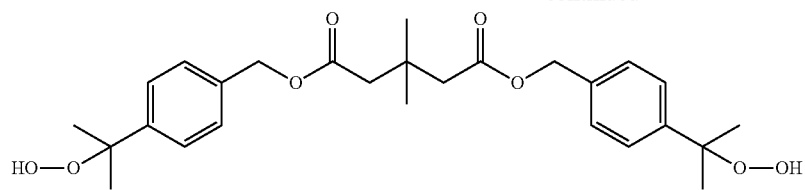
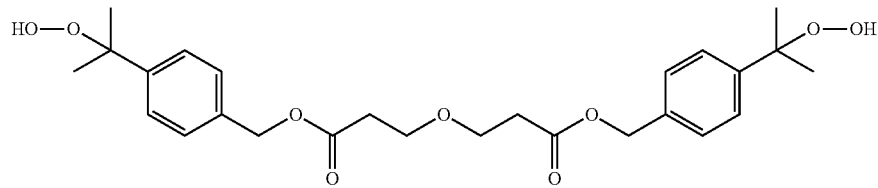
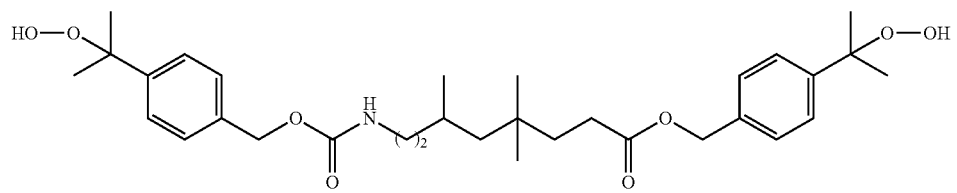
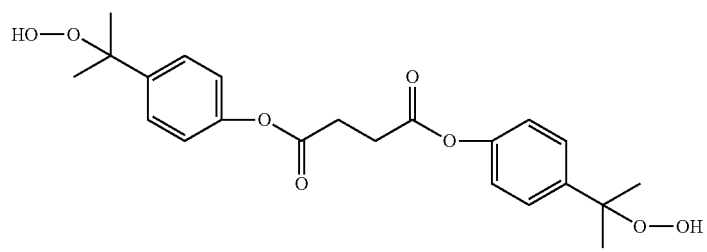
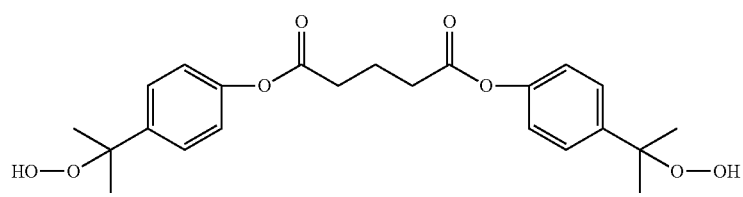
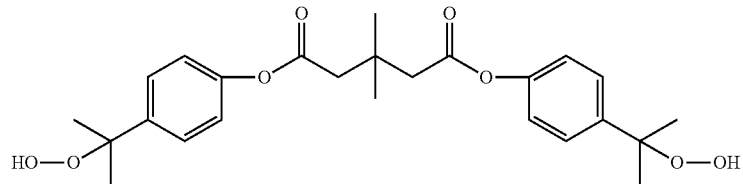
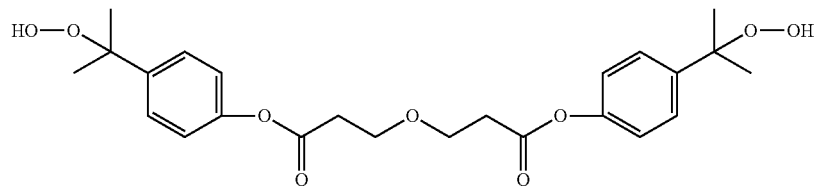
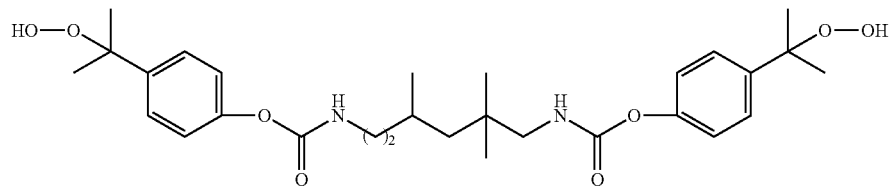

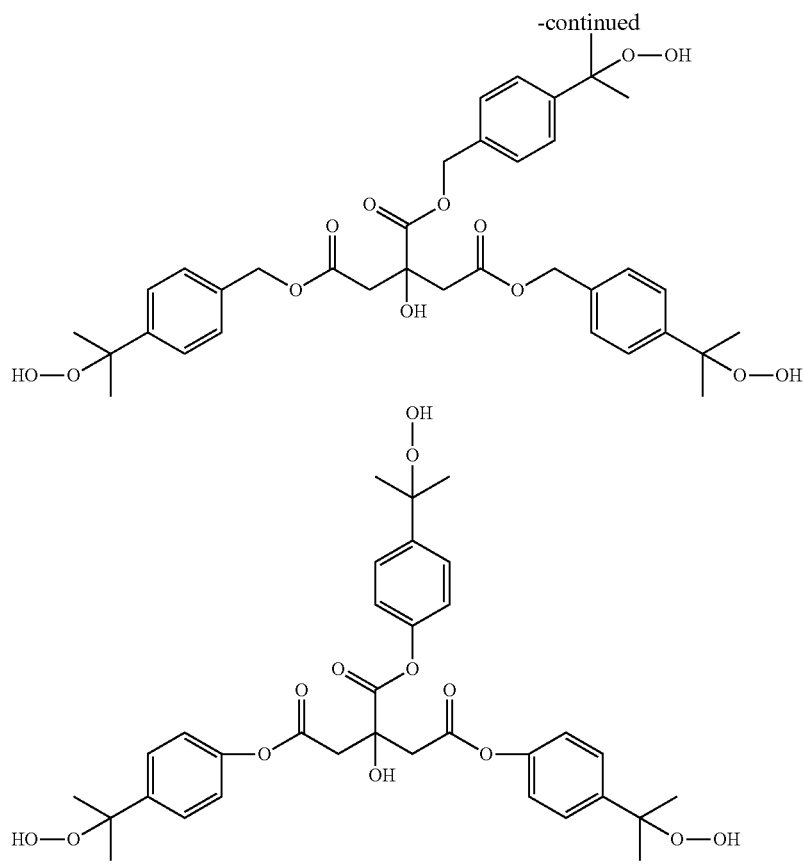

The hydroperoxide derivatives of Formula I display a great storage stability at room temperature and are particularly suitable as low-odour hydroperoxide component in redox initiator systems for dental compositions. The materials according to the invention can contain one or more hydroperoxides of Formula I.

The materials according to the invention contain at least one thiourea derivative in addition to the hydroperoxide of Formula (I). Thiourea derivatives preferred according to the invention are the compounds listed in paragraph [0009] in EP 1 754 465 A1. Particularly preferred thiourea derivatives are acetyl, allyl, pyridyl and phenyl thiourea, hexanoyl thiourea and mixtures thereof. Acetyl thiourea (ATU) is quite particularly preferred.

Thiourea derivatives with the formula

in which
X is H or Y,
Y is an alkyl radical with 1 to 8 carbon atoms, a cycloalkyl radical with 5 or 6 carbon atoms, a chlorine-, hydroxy- or mercapto-substituted alkyl radical with 1 to 8 carbon atoms, an alkenyl radical with 3 to 4 carbon atoms, an aryl radical with 6 to 8 carbon atoms, a chlorine-, hydroxy-, methoxy- or sulfonyl-substituted phenyl radical, an acyl radical with 2 to 8 carbon atoms, a chlorine- or methoxy-substituted acyl radical, an aral-kyl radical with 7 to 8 carbon atoms or a chlorine- or methoxy-substituted aralkyl radical, and
Z is $NH_2$, NHX or $NX_2$
are further preferred.

According to a preferred embodiment the dental materials according to the invention additionally contain at least one peroxide in addition to the hydroperoxide of Formula I and the thiourea derivative. It was surprisingly found that the reactivity of the initiator system based on a hydroperoxide of Formula I and a thiourea derivative can be considerably accelerated by the addition of a small quantity of a peroxide.

Peroxides preferred according to the invention are compounds of the formula $R^5—(O—O—R^6)_m$, in which $R^5$ and $R^6$ in each case represent an aliphatic or aromatic hydrocarbon radical or an acyl group and m is 1 or 2. Diacyl peroxides are particularly preferred. Preferred aliphatic hydrocarbon radicals are radicals with 3 to 8 carbon atoms, preferred aromatic hydrocarbon radicals are radicals with 6 to 12 carbon atoms, wherein benzene radicals which are substituted with 1 or 2 alkyl groups are particularly preferred. Preferred acyl groups are groups which contain 2 to 20 carbon atoms.

Preferred peroxides in which $R^5$ and $R^6$ in each case represent an aliphatic or aromatic hydrocarbon radical are α,α-bis(t-butylperoxy)diisopropylbenzene, dicumene peroxide, 2,5-dimethyl-2,5-bis(t-butylperoxy)hexane, t-butyl cumyl peroxide, di-t-butyl peroxide, 2,5-dimethyl-2,5-bis(t-butylperoxy)hexyne-3.

Preferred diacyl peroxides are isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide and mixtures thereof. A quite particularly preferred peroxide is benzoyl peroxide (DBPO). Hydroperoxides are not peroxides within the meaning of the invention.

According to a further preferred embodiment the dental materials according to the invention additionally contain at least one transition metal compound in addition to the hydroperoxide of Formula I and the thiourea derivative. It has been found that the addition of a transition metal compound yields materials which have significantly improved mechanical properties after hardening.

Transition metal compounds preferred according to the invention are compounds which are derived from transition metals which have at least two stable oxidation states. Compounds of the elements copper, iron, cobalt, nickel and manganese are particularly preferred. These metals have the following stable oxidation states: Cu(I)/Cu(II), Fe(II)/Fe(III), Co(II)/Co(III), Ni(II)/Ni(III), Mn(II)/Mn(III). Materials which contain at least one copper compound are particularly preferred.

The transition metals are preferably used in the form of their salts. Preferred salts are the nitrates, acetates, 2-ethylhexanoates and halides, wherein chlorides are particularly preferred.

The transition metals can furthermore advantageously be used in complexed form, wherein complexes with chelate-forming ligands are particularly preferred. Preferred simple ligands for complexing the transition metals are 2-ethylhexanoate and THF. Preferred chelate-forming ligands are 2-(2-aminoethylamino)ethanol, aliphatic amines, particularly preferably 1,1,4,7,10,10-hexamethyltriethylenetetramine (HMTETA), N,N,N',N'',N''-pentamethyldiethylenetriamine (PMDETA), tris[2-(dimethylamino)ethyl]amine (Me$_6$TREN), N,N,N',N'-tetramethylethylenediamine (TMEDA), 1,4,8,11-tetraaza-1,4,8,11-tetramethyl-cyclotetradecane (Me4CYCLAM), diethylenetriamine (DETA), triethylenetetramine (TETA) and 1,4,8,11-tetraazacyclotetradecane (CYCLAM); pyridine-containing ligands, particularly preferably N,N,N',N'-tetrakis(2-pyridylmethyl)ethylenediamine (TPEN), N, N-bis(2-pyridylmethyl)amine (BPMA), N,N-bis(2-pyridylmethyl)octylamine (BPMOA), 2,2'-bipyridine and 8-hydroxyquinoline. Quite particularly preferred ligands are acetylacetone, dimethylglyoxime and 1,10-phenanthroline.

In the case of electrically neutral ligands, the charge of the transition metal ions must be balanced by suitable counterions. For this, the above-named ions which are used to form salts are preferred wherein acetates and chlorides are particularly preferred. Chlorides and complexes are characterized by a relatively good solubility in monomers, which are used to prepare dental materials.

Instead of the transition metal complexes, non-complex salts of the transition metals in combination with complex-forming organic compounds can be used to prepare the dental materials, preferably in combination with the above-named chelate-forming compounds. The organic ligands form the catalytically active complexes when mixed with the transition metal salts. The use of such combinations of transition metal salts and organic ligands is preferred.

Transition metal compounds of the metals copper, iron, cobalt and nickel are preferred.

Preferred copper salts are CuCl, CuBr, CuCl$_2$, CuBr$_2$, CuI$_2$, Cu(II) carboxylates (e.g. of acetic acid or 2-ethylhexanoic acid). Preferred copper complexes are complexes with the ligands acetylacetone, phenanthroline (e.g. 1,10-phenanthroline (phen)), the aliphatic amines, such as e.g. 1,1,4,7,10,10-hexamethyltriethylenetetramine (HMTETA), N,N,N',N'',N''-pentamethyldiethylenetriamine (PMDETA), tris[2-(dimethylamino)ethyl]amine (Me$_6$TREN).

Preferred iron salts are FeCl$_3$, FeBr$_2$ and FeCl$_2$. Preferred iron complexes are complexes with the ligands acetylacetone, triphenylphosphine, 4,4'-di(5-nonyl)-2,2'-bipyridine (dNbpy) or 1,3-diisopropyl-4,5-dimethylimidazol-2-ylidene (Prilm). The complexes Fe(acac)$_2$ and FeCl$_2$(PPh$_3$)$_2$ are quite particularly preferred.

Preferred nickel salts are NiBr$_2$ and NiCl$_2$, preferred nickel complexes are nickel acetylacetonate and NiBr$_2$(PPh$_3$)$_2$.

In all cases, those complexes in which the respective transition metal is present in its most stable oxidation state are preferred. Complexes of Cu$^{2+}$, Fe$^{3+}$, Ni$^{2+}$ and Co$^{3+}$ are thus preferred.

According to the invention, copper compounds, copper complexes and in particular mixtures of copper salts and complexing organic ligands are particularly preferred.

Materials which contain at least one hydroperoxide of Formula I, at least one thiourea derivative, at least one peroxide and a transition metal compound, wherein these components are preferably in each case selected from the above-defined preferred and particularly preferred substances, are quite particularly preferred.

The hydroperoxide is preferably used in a quantity of from 0.01 to 10 wt.-%, particularly preferably 0.05 to 8.0 wt.-% and quite particularly preferably 0.1 to 5.0 wt.-%. The thiourea derivative is preferably used in a molar quantity of from 25 to 100 mol-%, preferably 50 to 100 mol-%, relative to the molar quantity of hydroperoxide, quite particularly preferably in the same molar concentration as the hydroperoxide.

The peroxide is, where applicable, preferably used in a quantity of from 1 to 15 wt.-%, preferably 1 to 10 wt.-% and quite particularly preferably from 2 to 8 wt.-%, relative to the mass of the hydroperoxide.

The transition metal compound is, where applicable, preferably used in a quantity of from 0.0001 to 1 wt.-%, preferably 0.0005 to 0.5 wt.-% and particularly preferably 0.0007 to 0.020 wt.-%, relative to the total mass of the composition.

Hydroperoxides of Formula (I) are particularly suitable for curing radically polymerizable compositions.

The materials according to the invention preferably contain at least one radically polymerizable monomer. Compositions which contain at least one mono- or multifunctional (meth)acrylate as radically polymerizable monomer are particularly preferred. By monofunctional (meth)acrylates is meant compounds with one, by multifunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates. Materials which are to be hardened intraorally preferably contain mono- and/or multifunctional methacrylates as radically polymerizable monomer.

Preferred mono- or multifunctional (meth)acrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), 2-(2-biphenyloxy)ethyl methacrylate, bisphenol A dimethacrylate, bis-GMA (an addition product of methacrylic acid and bisphenol A diglycidyl ether), ethoxylated or propoxylated bisphenol A dimethacrylate, such as e.g. 2-[4-(2-methacryloyloxyethoxyethoxy)phenyl]-2-[4-(2-methacryloyloxyethoxy)phenyl]propane (SR-348c, from Sartomer; contains 3 ethoxy groups) and 2,2-bis[4-(2-methacryloxypropoxy)phenyl]propane, UDMA (an addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol $\alpha,\alpha,\alpha',\alpha'$-tetramethyl-m-xylylene diisocyanate), di-, tri- or tetraethylene glycol dimethacrylate, trimethylolpropane trimethacrylate, pentaerythritol tetramethacrylate as well as glycerol di- and trimethacrylate, 1,4-butanediol dimethacrylate, 1,10-decanediol dimethacrylate ($D_3MA$), bis(methacryloyloxymethyl)tricyclo-[5.2.1.02.6]decane (DCP), polyethylene glycol or polypropylene glycol dimethacrylates, such as e.g. polyethylene glycol 200 dimethacrylate or polyethylene glycol 400 dimethacrylate (PEG 200 DMA or PEG 400 DMA) or 1,12-dodecanediol dimethacrylate, or a mixture thereof.

According to an embodiment the compositions according to the invention preferably additionally contain one or more acid-group-containing radically polymerizable monomers (adhesive monomers) in addition to the above-named monomers. These give the materials self-adhesive and/or self-etching properties. Acid-group-containing monomers are therefore particularly suitable for the preparation of self-adhesive dental materials, such as e.g. fixing cements.

Preferred acid-group-containing monomers are polymerizable carboxylic acids, phosphonic acids and phosphoric acid esters as well as their anhydrides. Preferred carboxylic acids and carboxylic acid anhydrides are 4-(meth)acryloyloxyethyl trimellitic acid anhydride, 10-methacryloyloxydecylmalonic acid, N-(2-hydroxy-3-methacryloyloxypropyl)-N-phenylglycine, 4-vinylbenzoic acid. Preferred phosphoric acid esters are 2-methacryloyloxyethylphenyl hydrogen phosphate, 10-methacryloyloxydecyl dihydrogen phosphate (MDP) and dipentaerythritol pentamethacryloyloxyphosphate. Preferred phosphonic acids are 4-vinylbenzylphosphonic acid, 2-[4-(dihydroxyphosphoryl)-2-oxabutyl]-acrylic acid and their amides, esters, such as e.g. 2-[4-(dihydroxyphosphoryl)-2-oxa-butyl]-acrylic acid-2,4,6-trimethylphenyl ester.

Particularly preferred acid-group-containing monomers are 4-vinylbenzylphosphonic acid, 2-[4-(dihydroxyphosphoryl)-2-oxa-butyl]-acrylic acid and their amides, esters, such as e.g. 2-[4-(dihydroxyphosphoryl)-2-oxa-butyl]-acrylic acid-2,4,6-trimethylphenyl ester, (meth)acrylamide dihydrogen phosphates, such as e.g. 6-methacrylamidohexyl- or 1,3-bis(methacrylamido)-propan-2-yl-dihydrogen phosphate, and mixtures thereof. These particularly preferred acid-group-containing monomers are characterized by a high hydrolytic stability.

The compositions according to the invention can advantageously additionally contain an initiator for the radical photopolymerization in addition to the initiator system according to the invention. Such compositions are dual-curing, i.e. they can be cured both chemically and by light. Preferred photoinitiators are benzophenone, benzoin as well as their derivatives, $\alpha$-diketones and their derivatives, such as 9,10-phenanthrenequinone, 1-phenyl-propane-1,2-dione, diacetyl and 4,4'-dichlorobenzil. Camphorquinone (CQ) and 2,2-dimethoxy-2-phenyl-acetophenone in combination with amines as reducing agent, such as e.g. 4-(dimethylamino)-benzoic acid ethyl ester (EDMAB), or N,N-dimethylaminoethyl methacrylate, are preferably used.

Compositions which do not contain amines are preferred according to the invention. Norrish type I photoinitiators are therefore particularly preferred. Norrish type I photoinitiators do not require an amine component.

Preferred Norrish type I photoinitiators are acyl- or bisacylphosphine oxides. Monoacyltrialkylgermane, diacyldialkylgermane and tetraacylgermane compounds, such as e.g. benzoyltrimethylgermane, dibenzoyldiethylgermane, bis(4-methoxybenzoyl)diethylgermane (Ivocerin®), tetrabenzoylgermane and tetrakis(o-methylbenzoyl)germane are particularly preferred.

Moreover, mixtures of the different photoinitiators can also be used, such as e.g. bis(4-methoxybenzoyl)diethylgermane or tetrakis(o-methylbenzoyl)germane in combination with camphorquinone and 4-dimethylaminobenzoic acid ethyl ester.

The dental materials according to the invention can moreover advantageously contain one or more organic or inorganic fillers. Particulate fillers are preferred. Filler-containing compositions are particularly suitable as dental fixing cements or filling composites.

Preferred inorganic fillers are oxides, such as $SiO_2$, $ZrO_2$ and $TiO_2$ or mixed oxides of $SiO_2$, $ZrO_2$, ZnO and/or $TiO_2$, nanoparticulate or microfine fillers, such as pyrogenic silica or precipitated silica, glass powders, such as quartz, glass ceramic, borosilicate or radiopaque glass powders, preferably barium or strontium aluminium silicate glasses, and radiopaque fillers, such as ytterbium trifluoride, tantalum(V) oxide, barium sulfate or mixed oxides of $SiO_2$ with ytterbium(III) oxide or tantalum(V) oxide. The dental materials according to the invention can furthermore contain fibrous fillers, nanofibres, whiskers or mixtures thereof.

Preferably, the oxides have a particle size of from 0.010 to 15 μm, the nanoparticulate or microfine fillers have a particle size of from 10 to 300 nm, the glass powders have a particle size of from 0.01 to 15 μm, preferably of from 0.2 to 1.5 μm, and the radiopaque fillers have a particle size of from 0.2 to 5 μm.

Particularly preferred fillers are mixed oxides of $SiO_2$ and $ZrO_2$, with a particle size of from 10 to 300 nm, glass powders with a particle size of from 0.2 to 1.5 μm, in particular radiopaque glass powders of e.g. barium or strontium aluminium silicate glasses, and radiopaque fillers with a particle size of from 0.2 to 5 μm, in particular ytterbium trifluoride and/or mixed oxides of $SiO_2$ with ytterbium(III) oxide.

Moreover, ground prepolymers or pearl polymers (isofillers) are suitable as filler. These can consist exclusively of organic polymers, or organic polymers which themselves are filled with inorganic fillers such as radiopaque glass powder(s) and ytterbium trifluoride. The above-defined monomers and fillers are suitable for the preparation of the ground prepolymers and pearl polymers. Compositions for the production of full dentures preferably contain as fillers exclusively organic fillers, particularly preferably ground polymers or pearl polymers based on polymethyl methacrylate (PMMA), quite particularly preferably pearl polymers based on PMMA.

Unless otherwise stated, all particle sizes are weight-average particle sizes, wherein the particle-size determination in the range of from 0.1 μm to 1000 μm is effected by means of static light scattering, preferably using an LA-960 static laser scattering particle size analyzer (Horiba, Japan). Here, a laser diode with a wavelength of 655 nm and an LED with a wavelength of 405 nm are used as light sources. The use of two light sources with different wavelengths makes it possible to measure the entire particle-size distribution of a sample in only one measurement pass, wherein the measurement is carried out as a wet measurement. For this, a 0.1 to 0.5% aqueous dispersion of the filler is prepared and the scattered light thereof is measured in a flow cell. The scattered-light analysis for calculating particle size and particle-size distribution is effected in accordance with the Mie theory according to DIN/ISO 13320.

Particle sizes smaller than 0.1 μm are preferably determined by means of dynamic light scattering (DLS). The measurement of the particle size in the range of from 5 nm to 0.1 μm is preferably effected by dynamic light scattering (DLS) of aqueous particle dispersions, preferably with a Malvern Zetasizer Nano ZS (Malvern Instruments, Malvern UK) with an He—Ne laser with a wavelength of 633 nm, at a scattering angle of 90° at 25° C.

Particle sizes smaller than 0.1 μm can also be determined by means of SEM or TEM spectroscopy. The transmission electron microscopy (TEM) is preferably carried out with a Philips CM30 TEM at an accelerating voltage of 300 kV. For the preparation of the samples, drops of the particle dispersion are applied to a 50 Å thick copper grid (mesh size 300), which is coated with carbon, and then the solvent is evaporated.

The light scattering decreases as the particle size decreases, but fillers with a small particle size have a greater thickening action. The fillers are divided according to their particle size into macrofillers and microfillers, wherein fillers with an average particle size of from 0.2 to 10 μm are called macrofillers and fillers with an average particle size of from approx. 5 to 100 nm are called microfillers. Macrofillers are obtained e.g. by grinding e.g. quartz, radiopaque glasses, borosilicates or ceramic and usually consist of splintery parts. Microfillers such as mixed oxides can be prepared e.g. by hydrolytic co-condensation of metal alkoxides.

To improve the bond between the filler particles and the crosslinked polymerization matrix, the fillers are preferably surface-modified, particularly preferably by silanization, quite particularly preferably by radically polymerizable silanes, in particular with 3-methacryloyloxypropyltrimethoxysilane. For the surface-modification of non-silicate fillers, e.g. of $ZrO_2$ or $TiO_2$, functionalized acidic phosphates, such as e.g. 10-methacryloyloxydecyl dihydrogen phosphate can also be used.

Moreover, the dental materials according to the invention can contain one or more further additives, preferably stabilizers, colorants, microbiocidal active ingredients, fluoride-ion-releasing additives, foaming agents, optical brighteners, plasticizers and/or UV absorbers.

Dental materials which contain
(a) 0.01 to 10 wt.-%, preferably 0.05 to 8.0 wt.-% and particularly preferably 0.1 to 3.0 wt.-% hydroperoxide of Formula (I),
(b) 0.001 to 5.0 wt.-%, preferably 0.003 to 4.0 wt.-%, particularly preferably 0.005 to 3.0 wt.-% thiourea and/or thiourea derivative,
(c) 5 to 95 wt.-%, preferably 10 to 95 wt.-% and particularly preferably 10 to 90 wt.-% radically polymerizable monomer,
(d) 0 to 85 wt.-% filler, and
(e) 0.01 to 5 wt.-%, preferably 0.1 to 3 wt.-% and particularly preferably 0.1 to 2 wt.-% additive
are preferred according to the invention.

All quantities herein are relative to the total mass of the composition, unless otherwise stated.

The filling level is geared towards the desired intended use of the material. Preferably filling composites have a filler content of from 50 to 85 wt.-%, particularly preferably 70 to 80 wt.-%, and dental cements have a filler content of from 10 to 70 wt.-%, particularly preferably 60 to 70 wt.-%.

Dental materials which additionally contain (f) 0.001 to 3.0 wt.-%, preferably 0.005 to 2.0 wt.-% and particularly preferably 0.005 to 0.50 wt.-% peroxide, preferably DBPO,
and/or
(g) 0.0001 to 1 wt.-%, preferably 0.0005 to 0.5 wt.-%, particularly preferably 0.0007 to 0.02 wt.-% transition metal compound are particularly preferred.

Dental materials for the production of complete dentures preferably have the following composition:
(a) 0.01 to 5.0 wt.-%, preferably 0.05 to 4.0 wt.-% and particularly preferably 0.1 to 3.0 wt.-% hydroperoxide of Formula (I),
(b) 0.001 to 5.0 wt.-%, particularly preferably 0.005 to 2.0 wt.-% thiourea and/or thiourea derivative,
(c) 20 to 95 wt.-%, preferably 30 to 95 wt.-% and particularly preferably 40 to 95 wt.-% radically polymerizable monomer,
(d) 5 to 80 wt.-%, preferably 10 to 70 wt.-% and particularly preferably 20 to 60 wt.-% isofiller,
(e) 0.01 to 5 wt.-%, preferably 0.1 to 3 wt.-% and particularly preferably 0.1 to 2 wt.-% additive.

Those dental materials which consist of the named components are particularly preferred, wherein the individual components are preferably in each case selected from the above-named preferred and particularly preferred substances. In all cases, a mixture of several substances, thus for example a mixture of monomers, can also be used as respective component.

The compositions according to the invention are particularly suitable as dental materials, in particular as dental cements, filling composites and veneering materials as well as materials for the production of prostheses, artificial teeth, inlays, onlays, crowns and bridges. The compositions are suitable primarily for intraoral application by the dentist for the restoration of damaged teeth, i.e. for therapeutic application, e.g. as dental cements, filling composites and veneering materials. However, they can also be used non-therapeutically (extraorally), for example in the production or repair of dental restorations, such as prostheses, artificial teeth, inlays, onlays, crowns and bridges.

The compositions according to the invention are moreover suitable for the production of shaped bodies for dental, but also for non-dental purposes, which can be produced e.g. by means of casting, compression moulding and in particular by additive processes such as 3D printing.

The invention is explained in more detail in the following with reference to embodiment examples:

EXAMPLES

Example 1

Synthesis of 4-(2-hydroperoxypropan-2-yl)-phenylpropionate

1st Stage: (4-isopropylphenyl)-propionate (IPPP)

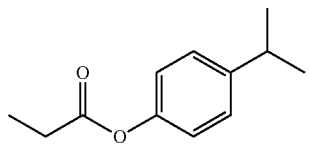

499.7 g (3.84 mol) propionic acid anhydride was added dropwise at 0° C. to a solution of 523.0 g (3.84 mol) 4-isopropylphenol, 388.6 g (3.84 mol) triethylamine and 46.9 g (0.38 mol) 4-dimethylaminopyridine in 4.50 l dichloromethane. The mixture was allowed to slowly warm up to room temperature. After a total reaction time of 15 h the solution was washed as follows: twice with 1.50 l 1 N hydrochloric acid each time, twice with 1.50 l 1 N sodium hydroxide solution each time and twice with 1.50 l water each time. After drying the organic phase with anhydrous sodium sulfate, the solvent was distilled off completely. 699.8 g (95%) IPPP was obtained as a clear, colourless liquid in a purity of 98.82% (HPLC).

$n_D^{20}$: 1.4916

$^1$H NMR (400 MHz, CDCl$_3$): δ (ppm)=1.23 [d, J=7.0 Hz, 6H, HC(C$\underline{H}_3$)$_2$], 1.25 (t, J=7.6 Hz, 3H, CH$_2$C$\underline{H}_3$), 2.55 (t, J=7.6 Hz, 2H, C$\underline{H}_2$CH$_3$), 2.89 [September, J=7.0 Hz, 1H, $\underline{H}$C(CH$_3$)$_2$], 6.97-7.00 and 7.19-7.23 (2 m, each 2H, =CH).

$^{13}$C NMR (100 MHz, CDCl$_3$): δ (ppm)=9.13 (CH$_2\underline{C}$H$_3$), 24.1 [HC($\underline{C}$H$_3$)$_2$], 27.8 ($\underline{C}$H$_2$CH$_3$), 33.7 [H$\underline{C}$(CH$_3$)$_2$], 121.3 and 127.3 (=CH), 146.2 and 148.8 (=C), 173.1 (C=O).

IR (diamond ATR): ν (cm$^{-1}$)=2964 (m, C—H), 1758 (s, C=O), 1720 (m, C=C), 1604 and 1508 (m, s, aromatic compound), 1462 (m, CH$_2$, CH$_3$), 1352 (m, CH$_3$), 1200 and 1148 (vs, COC), 836 (m, =CH).

2nd Stage:
4-(2-hydroperoxypropan-2-yl)-phenylpropionate
(IPPPHP)

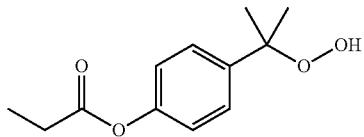 [SMILES: CCC(=O)Oc1ccc(C(C)(C)OO)cc1]

33.3 g (0.173 mol) IPPP and 2.82 g (0.017 mol) N-hydroxyphthalimide were dissolved in 600 ml acetonitrile, warmed to 30° C. and a stream of oxygen was passed through the solution for 10 min. After the addition of 2.60 g (0.009 mol) 2,2'-azobis-(4-methoxy-2,4-dimethylvaleronitrile) the reaction mixture was stirred for 5 days under an oxygen atmosphere at 30° C. After the solvent had been removed, a chromatographic purification of the crude product over silica gel (n-heptane/ethyl acetate 4:1) was effected. 8.90 g (23%)

IPPPHP was obtained as a clear, colourless, virtually odourless oil with a hydroperoxide content of 85% (titration).

$n_D^{20}$: 1.5100

$^1$H NMR (400 MHz, CDCl$_3$): δ (ppm)=1.25 (t, J=7.5 Hz, 3H, CH$_2$C$\underline{H}_3$), 1.57 (s, 6H, CH$_3$), 2.58 (t, J=7.5 Hz, 2H, C$\underline{H}_2$CH$_3$), 7.04-7.07 and 7.43-7.47 (2 m, each 2H, =CH), 7.75 (s, 1H, OOH).

$^{13}$C NMR (100 MHz, CDCl$_3$): δ (ppm)=9.06 (CH$_2\underline{C}$H$_3$), 26.1 [C($\underline{C}$H$_3$)$_2$], 27.7 ($\underline{C}$H$_2$CH$_3$), 83.5 [$\underline{C}$(CH$_3$)$_2$], 121.4 and 126.7 (=CH), 142.2 and 149.9 (=C), 173.2 (C=O).

IR (diamond ATR): ν (cm$^{-1}$)=3416 (m, OH), 2983 (m, C—H), 1758 (s, C=O), 1725 (s, C=C), 1605 and 1507 (m, s, aromatic compound), 1462 (m, CH$_2$, CH$_3$), 1360 (m, CH$_3$), 1201 and 1148 (vs, COC), 834 (m, =CH).

Example 2

4-(2-Hydroperoxypropan-2-yl)-benzyl-(4-isopropylbenzyl)-succinate (HPS)

1st Stage: Synthesis of
bis-(4-isopropylbenzyl)-succinate

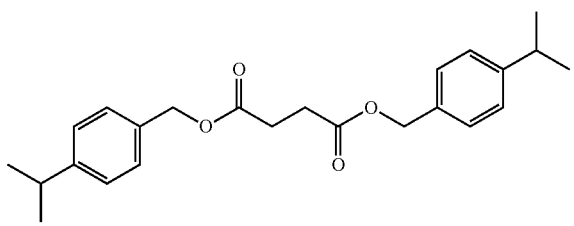 [SMILES: CC(C)c1ccc(COC(=O)CCC(=O)OCc2ccc(C(C)C)cc2)cc1]

A solution of 61.9 g (0.30 mol) N,N'-dicyclohexylcarbodiimide (DCC) in 250 ml dichloromethane was added dropwise at 0° C. to a solution of 78.4 g (0.522 mol) 4-isopropylbenzyl alcohol, 30.8 g (0.261 mol) succinic acid and 1.59 g (0.013 mol) DMAP in 0.35 l dichloromethane. The reaction mixture was stirred for 18 h at room temperature, then a further 1.60 g (0.013 mol) DMAP and 8.00 g (0.039 mol) DCC were added and the mixture was stirred for a further 5 days at room temperature. After the solid constituents had been filtered off, the filtrate was washed 3× with 150 ml 2N hydrochloric acid each time, 3× with 150 ml 2N sodium hydroxide solution each time and 3× with 150 ml saturated sodium chloride solution each time, dried with anhydrous sodium sulfate and concentrated. The further purification was effected by chromatography over silica gel with n-heptane/ethyl acetate (3:1) as eluent. After the concentration 40.5 g (41%) bis-(4-isopropylbenzyl)-succinate was obtained as a clear, colourless liquid.

$n_D^{20}$: 1.5249

$^1$H NMR (400 MHz, CDCl$_3$): δ (ppm)=1.23 [d, J=6.9 Hz, 12H, HC(C$\underline{H}_3$)$_2$], 2.68 (s, 4H, O=C—CH$_2$), 2.90 [September, J=6.9 Hz, 2H, $\underline{H}$C(CH$_3$)$_2$], 5.08 (s, 4H, OCH$_2$), 7.20-7.27 (m, 8H, =CH).

$^{13}$C NMR (100 MHz, CDCl$_3$): δ (ppm)=24.0 [HC($\underline{C}$H$_3$)$_2$], 29.2 (O=C—$\underline{C}$H$_2$), 33.9 [H$\underline{C}$(CH$_3$)$_2$], 66.6 (OCH$_2$), 126.7 and 128.5 (=CH), 133.2 (=C—CH$_2$O), 149.1 (=C—CH), 172.1 (C=O).

IR (diamond ATR): ν (cm$^{-1}$)=2960 (m, C—H), 1733 (vs, C=O), 1615 and 1515 (w, m, aromatic compound), 1463 (m, CH$_2$, CH$_3$), 1349 (m, CH$_3$), 1149 (vs, COC), 817 (s, =CH).

2nd Stage: Synthesis of 4-(2-hydroperoxypropan-2-yl)-benzyl-(4-isopropylbenzyl)-succinate (HPS)

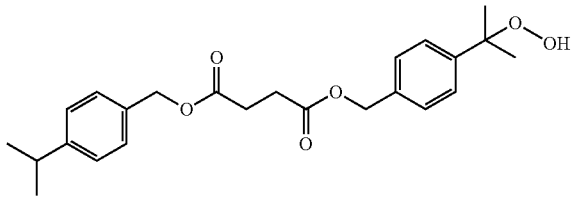 [SMILES: CC(C)c1ccc(COC(=O)CCC(=O)OCc2ccc(C(C)(C)OO)cc2)cc1]

20.0 g (52.3 mmol) bis-(4-isopropylbenzyl)-succinate and 0.85 g (5.23 mmol) N-hydroxyphthalimide were dissolved in 300 ml acetonitrile, warmed to 30° C. and a stream of oxygen was passed through the solution for 10 min. After the addition of 0.78 g (2.61 mmol) 2,2'-azobis-(4-methoxy-2,4-dimethylvaleronitrile) the reaction mixture was stirred for 6 days under an oxygen atmosphere at 30° C. After the solvent had been removed, the residue was taken up in 15 ml dichloromethane and filtered off from the precipitated solid. After the dichloromethane had been removed, a chromatographic purification of the crude product over silica gel (n-heptane/ethyl acetate 3:1) was effected. 3.34 g (14%) HPS was obtained as a colourless, almost odourless oil with a hydroperoxide content of 95.5% (titration).

$n_D^{20}$: 1.5314

$^1$H NMR (400 MHz, CDCl$_3$): δ (ppm)=1.24 [d, J=7.0 Hz, 6H, HC(C$\underline{H}_3$)$_2$], 1.59 (s, 6H, OC(CH$_3$)$_2$], 2.69 (s, 4H, O=C—C$\underline{H}_2$), 2.90 [September, J=6.9 Hz, 1H, $\underline{H}$C(CH$_3$)$_2$], 5.08 and 5.10 (2 s, each 2H, OCH$_2$), 7.20-7.27 and 7.33-7.46 (2 m, each 4H, =CH).

$^{13}$C NMR (100 MHz, CDCl$_3$): δ (ppm)=23.9 [HC($\underline{C}$H$_3$)$_2$], 26.1 [OC($\underline{C}$H$_3$)$_2$], 29.2 (O=C—$\underline{C}$H$_2$), 33.9 [H$\underline{C}$(CH$_3$)$_2$], 66.2 and 66.6 (OCH$_2$), 83.8 [O$\underline{C}$(CH$_3$)$_2$], 125.7, 126.6, 128.4 and 128.5 (=CH), 133.2 and 134.9 (=C—CH$_2$O), 144.9 (=$\underline{C}$—CO), 149.1 (=C—CH), 172.1 and 172.2 (C=O).

IR (diamond ATR): ν (cm$^{-1}$)=3415 (br, OH), 2961 (m, C—H), 1733 (vs, C=O), 1610 and 1515 (w, m, aromatic compound), 1462 (m, CH$_2$, CH$_3$), 1350 (m, CH$_3$), 1152 (vs, COC), 818 (s, =CH).

Example 3

Composite Cement Based on the Hydroperoxide IPPPHP From Example 1

Chemically curing composite cements, in each case consisting of a base paste and a catalyst paste according to Table 1, were prepared by mixing the dimethacrylates UDMA (addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), DCP (bis(methacryloyloxymethyl)tricyclo-[5.2.1.0$^{2,6}$]decane) and PEG 400 DMA (polyethylene glycol 400 dimethacrylate), the stabilizer BHT (2,6-di-tert-butyl-4-methylphenol), the pyrogenic silicas HDK 2000 (Wacker) and Aerosil OX-50 (Evonik) as well as the initiator components cumene hydroperoxide (Merck, CHP) and IPPPHP, copper (II) acetylacetonate (Cuacac) and hexanoyl thiourea (HTH).

TABLE 1

Composition of the catalyst pastes Cat-1 and Cat-2 and of the base pastes Base-1 and Base-2 (figures in wt.-%)

| Component | Cat-1 | Cat-2 | Base-1 | Base-2 |
| --- | --- | --- | --- | --- |
| UDMA | 19.75 | 19.99 | 20.93 | 20.90 |
| V-380 | 11.05 | 11.16 | 11.41 | 11.39 |
| DCP | 6.89 | 6.99 | 7.12 | 7.13 |
| PEG 400 DMA | 8.27 | 8.37 | 8.54 | 8.54 |
| HDK 2000 | 3.50 | 3.50 | 3.50 | 3.50 |
| Aerosil OX 50 | 47.99 | 48.01 | 47.96 | 48.01 |
| BHT | 0.05 | 0.05 | 0.10 | 0.10 |
| CHP (80%) | 2.50 | — | — | — |
| IPPPHP (8%) | — | 1.94 | — | — |
| HTA | — | — | 0.49 | 0.49 |
| Cuacac | — | — | 0.03 | 0.03 |

The pastes Cat-1 and Base-1, and Cat-2 and Base-2, were blended in each case in a 1:1 volume ratio using a double-push syringe with mixing tip and the processing time and mechanical properties of the obtained cements C-1 and C-2 were determined. The processing time and mechanical properties were determined according to the EN ISO-4049 standard (Dentistry—Polymer-based filling, restorative and luting materials). To determine the processing time PT, immediately after mixing the pastes were introduced into the test tube of an exothermic apparatus with thermocouple (thermocouple type K (Thermocoax FKI 10/50NN); manufacturer: THERMOCONTROL GmbH, Dietikon/Switzerland), wherein the time measurement started with the beginning of mixing. The beginning of the curing is associated with a temperature increase, which the exothermic apparatus indicates with a rising curve. The point in time of the temperature rise corresponds to the beginning of the curing reaction and thus the end of the processing time. The processing time is the time phase from the beginning of mixing to the beginning of curing. To determine the mechanical properties, test pieces were produced and their flexural strength FS and flexural modulus of elasticity were determined according to the EN ISO-4049 standard. The mechanical properties were measured after 24 h storage of the test pieces in water (WS) at 37° C. The results are specified in Table 2.

TABLE 2

Processing time (PT, s), flexural strength (FS, MPa) and flexural modulus of elasticity (FM, GPa) of the cements C-1 and C-2

| Cement | PT | FS | Flexural modulus of elasticity |
| --- | --- | --- | --- |
| C-1 (Cat-1 + Base-1)*[)] | 49 | 143 | 6.02 |
| C-2 (Cat-2 + Base-2) | 57 | 123 | 5.58 |

*[)]Comparison example

The results prove that the cement C-2 based on the virtually odour-free cumene hydroperoxide IPPPHP from Example 1 displays properties comparable to those of the cement C1 based on the very strongly odorous cumene hydroperoxide CHP.

Example 4

Composite Cement Based on the Hydroperoxide HPS From Example 2

A chemically curing composite cement with the base paste Base-3 and the catalyst paste Cat-3 was prepared from a mixture of the dimethacrylates UDMA, SR-348c (ethoxylated bisphenol A dimethacrylate with 3 ethoxy groups) and DCP, the stabilizer BHT (2,6-di-tert-butyl-4-methylphenol), the pyrogenic silicas HDK 200 (Wacker) and SG-So100 (Sukgyung) as well as the initiator components HPS (from Example 2), copper(I) chloride (CuCl), hexanoyl thiourea (HTH) and 2-mercaptobenzimidazole (2-MBI) (Table 3).

TABLE 3

Composition of the catalyst paste Cat-3 and of the base paste Base-3 (figures in wt.-%)

| Component | Cat-3 | Base-3 |
| --- | --- | --- |
| UDMA | 17.84 | 19.475 |
| SR-348C | 22.31 | 23.73 |
| DCP | 4.47 | 4.75 |

TABLE 3-continued

Composition of the catalyst paste Cat-3 and of the base paste Base-3 (figures in wt.-%)

| Component | Cat-3 | Base-3 |
|---|---|---|
| HDK2000 | 3.02 | 3.0 |
| SG-Sol 100 | 48.00 | 48.00 |
| BHT | 0.05 | 0.05 |
| HPS (92%) | 4.31 | — |
| 2-MBI | — | 0.49 |
| HTH | — | 0.49 |
| CuCl | — | 0.015 |

Test pieces were produced analogously to Example 3 and the processing time PT and the mechanical properties were determined (Table 4).

TABLE 4

Processing time (PT, s), flexural strength (FS, MPa) and flexural modulus of elasticity (FM, GPa) of the cement C-3

| Cement | PT | FS | Flexural modulus of elasticity |
|---|---|---|---|
| C-3 (Cat-3 + Base-3) | 35 | 103 | 3.96 |

The invention claimed is:

1. Radically polymerizable dental material comprising a combination of a thiourea derivative and a hydroperoxide as an initiator system for the radical polymerization, characterized in that it contains a hydroperoxide according to the following Formula (I),

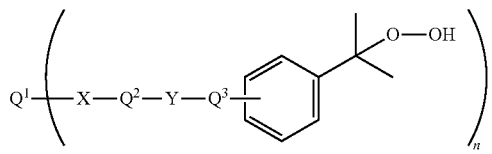

Formula I in which the variables have the following meanings:
Q$^1$ an n-valent, aromatic, aliphatic, linear or branched C$_1$-C$_{14}$ hydrocarbon radical, which can be interrupted by one or more S and/or O atoms and which can be unsubstituted or substituted by one or more substituents,
X, Y independently of each other are in each case absent, —O—, —COO—; —CONR$^2$—, or —O—CO—NR$^3$—, wherein R$^2$ and R$^3$ independently of each other represent H or a C$_1$-C$_5$ alkyl radical,
Q$^2$ is absent with, an aliphatic, linear or branched C$_1$-C$_{14}$ alkylene radical, which can be interrupted by S and/or O atoms and which can be unsubstituted or substituted by —OH, —OR$^4$, —Cl and/or —Br, wherein R$^4$ is an aliphatic, linear or branched C$_1$-C$_{10}$ hydrocarbon radical,
Q$^3$ a C$_1$-C$_3$ alkylene group or is absent,
wherein X and/or Y is absent if Q$^2$ is absent,
n 1, 2, 3 or 4, and wherein
the substitution on the aromatic compound takes place in position 2, 3 or 4.

2. Dental material according to claim 1, in which the variables have the following meanings:
Q$^1$ an n-valent, aromatic, aliphatic, linear or branched C$_1$-C$_{14}$ hydrocarbon radical, which can be interrupted by one or more S and/or O atoms and which can be unsubstituted or substituted by one or more substituents which are selected from —OH, —OR$^1$, —Cl and —Br, wherein R$^1$ is an aliphatic, linear or branched C$_1$-C$_{10}$ hydrocarbon radical,
X, Y independently of each other are in each case absent, —O—, —COO—; —CONR$^2$—, or —O—CO—NR$^3$—, wherein R$^2$ and R$^3$ independently of each other represent H, methyl and/or ethyl, and wherein X and Y are not absent at the same time,
Q$^2$ is absent with, an aliphatic, linear or branched C$_1$-C$_{14}$ alkylene radical, which can be interrupted by S and/or O atoms and which can be unsubstituted or substituted by —OH, —OR$^4$, —Cl and/or —Br, wherein R$^4$ is an aliphatic, linear or branched C$_1$-C$_{10}$ hydrocarbon radical,
Q$^3$ -CH$_2$— or is absent
wherein X and/or Y is absent if Q$^2$ is absent,
n 1, 2, 3 or 4, and wherein
the substitution on the aromatic compound takes place in position 2, 3 or 4.

3. Dental material according to claim 1, in which the variables have the following meanings:
Q$^1$ a mono- or divalent, aliphatic, linear or branched C$_1$-C$_{10}$ hydrocarbon radical, which can be interrupted by one or more O atoms, and which can be substituted by one or more substituents which are selected from —OH and —OR$^1$, or is unsubstituted, wherein R$^1$ is an aliphatic, linear or branched C$_1$-C$_6$ hydrocarbon radical,
X, Y independently of each other are in each case absent, —O—, —COO— or —O—CO—NR$^3$—, wherein R$^3$ represents H or a C$_1$-C$_5$ alkyl radical,
Q$^2$ is absent with, a linear or branched C$_1$-C$_{10}$ alkylene radical, which can be interrupted by one or more O atoms, and which can be substituted by one or more substituents which are selected from —OH and —OR$^4$, or is unsubstituted, wherein R$^4$ is an aliphatic, linear or branched C$_1$-C$_6$ hydrocarbon radical,
n 1 or 2, and wherein
the substitution on the aromatic compound takes place in position 3 or in position 4.

4. Dental material according to claim 1, in which the variables have the following meanings:
Q$^1$ a mono- or divalent, aliphatic, linear or branched C$_1$-C$_{10}$ hydrocarbon radical, which can be interrupted by one O atom, and which can be substituted by one substituent which is selected from —OH and —OR$^1$, or is unsubstituted, wherein R$^1$ is an aliphatic, linear or branched C$_1$-C$_6$ hydrocarbon radical,
X, Y independently of each other are in each case absent, —O—, —COO— or —O—CO—NR$^3$—, wherein R$^3$ represents H, methyl and/or ethyl and wherein X and Y are not absent at the same time,
Q$^2$ is absent with, a linear or branched C$_1$-C$_{10}$ alkylene radical, which can be interrupted by one O atom, and which can be substituted by one substituent which is selected from —OH and —OR$^4$, or is unsubstituted, wherein R$^4$ is an aliphatic, linear or branched C$_1$-C$_6$ hydrocarbon radical,
n 1 or 2, and wherein
the substitution on the aromatic compound takes place in in position 4.

5. Dental material according to claim 3, in which the variables have the following meanings:
- $Q^1$ a mono- or divalent, aliphatic, linear or branched $C_1$-$C_5$ hydrocarbon radical, which can be interrupted by one O atom and which can be substituted by one OH group,
- X —COO—,
- Y is absent
- $Q^2$ is absent or a linear $C_1$-$C_3$ alkylene radical,
- n 1 or 2, and wherein
- the substitution on the aromatic compound takes place in position 4.

6. Dental material according to claim 5, in which the variables have the following meanings:
- $Q^1$ a mono- or divalent, aliphatic, branched, or linear $C_1$-$C_4$ hydrocarbon radical,
- X —COO—,
- Y is absent
- $Q^2$ is absent or a methylene radical,
- n 1 or 2, and wherein
- the substitution on the aromatic compound takes place in position 4.

7. Dental material according to claim 1, comprising acetyl, allyl, pyridyl, phenyl thiourea, hexanoyl thiourea, or a mixture thereof, as thiourea derivative.

8. Dental material according to claim 1, which additionally comprises a peroxide.

9. Dental material according to claim 8, wherein the peroxide comprises α,α-bis(t-butylperoxy)diisopropylbenzene, dicumene peroxide, 2,5-dimethyl-2,5-bis(t-butylperoxy)hexane, t-butyl cumyl peroxide, di-t-butyl peroxide, 2,5-dimethyl-2,5-bis(t-butylperoxy)hexyne-3 or a mixture thereof, a diacyl peroxide, isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide, benzoyl peroxide (DBPO) or a mixture thereof.

10. Dental material according to claim 1, which additionally comprises a transition metal compound.

11. Dental material according to claim 10, wherein the transition metal compound comprises a compound of a transition metal which has at least two stable oxidation states, or a compound of copper, iron, cobalt, nickel, manganese or a mixture thereof.

12. Dental material according to claim 1 comprising
- 0.01 to 10 wt.-% hydroperoxide, relative to the total mass of the material,
- 25 to 100 mol-% of thiourea derivative, relative to the molar quantity of hydroperoxide,
- optionally 1 to 15 wt.-% peroxide, relative to the mass of the hydroperoxide, and
- optionally 0.0001 to 1 wt.-% transition metal compound, relative to the total mass of the composition.

13. Dental material according to claim 1 comprising
- 0.05 to 8.0 wt.-% hydroperoxide, relative to the total mass of the material,
- 50 to 100 mol-% thiourea derivative, relative to the molar quantity of hydroperoxide,
- optionally 1 to 10 wt.-% peroxide, relative to the mass of the hydroperoxide, and
- optionally 0.0005 to 0.5 wt.-% transition metal compound, relative to the total mass of the composition.

14. Dental material according to claim 1 comprising
- 0.1 to 5.0 wt.-% hydroperoxide, relative to the total mass of the material,
- an equimolar quantity of thiourea derivative, relative to the molar quantity of hydroperoxide,
- optionally 2 to 8 wt.-% peroxide, relative to the mass of the hydroperoxide, and
- optionally 0.0007 to 0.020 wt.-% transition metal compound, relative to the total mass of the composition.

15. Dental material according to claim 1, which additionally comprises at least one radically polymerizable monomer or at least one mono- or multifunctional (meth)acrylate or at least one dimethacrylate or a mixture of mono- and dimethacrylates.

16. Dental material according to claim 15, which comprises methyl, ethyl, 2-hydroxyethyl, butyl, benzyl, tetrahydrofurfuryl or isobornyl (meth)acrylate, p-cumylphenoxyethylene glycol methacrylate (CMP-1E), 2-(2-biphenyloxy)ethyl methacrylate, bisphenol A dimethacrylate, bis-GMA (an addition product of methacrylic acid and bisphenol A diglycidyl ether), ethoxylated or propoxylated bisphenol A dimethacrylate, 2-[4-(2-methacryloyloxyethoxyethoxy)phenyl]-2-[4-(2-methacryloyloxyethoxy)phenyl]propane) (SR-348c), 2,2-bis[4-(2-methacryloxypropoxy)phenyl]propane, UDMA (an addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), di-, tri- or tetraethylene glycol dimethacrylate, trimethylolpropane trimethacrylate, pentaerythritol tetramethacrylate, glycerol di- and trimethacrylate, 1,4-butanediol dimethacrylate, 1,10-decanediol dimethacrylate ($D_3MA$), bis(methacryloyloxymethyl)tricyclo-[5.2.1.02.6]decane (DCP), a polyethylene glycol or polypropylene glycol dimethacrylate, polyethylene glycol 200 dimethacrylate, polyethylene glycol 400 dimethacrylate (PEG 200 DMA or PEG 400 DMA), 1,12-dodecanediol dimethacrylate or a mixture thereof as radically polymerizable monomer.

17. Dental material according to claim 15, which additionally comprises at least one acid-group-containing radically polymerizable monomer, a polymerizable carboxylic acid, phosphonic acid, a polymerizable phosphoric acid ester or an anhydride of these substances.

18. Dental material according to claim 1, which additionally comprises at least one of an organic or inorganic filler, an oxide, $SiO^2$, $ZrO^2$ and $TiO^2$ or a mixed oxide of $SiO^2$, $ZrO^2$, ZnO and/or $TiO^2$, a nanoparticulate or microfine filler, pyrogenic silica or precipitated silica, glass powder, quartz, glass ceramic or radiopaque glass powder, barium or strontium aluminium silicate glass powder, a radiopaque filler, ytterbium trifluoride, tantalum(V) oxide, barium sulfate, a mixed oxide of $SiO_2$ with ytterbium(III) oxide or tantalum (V) oxide, a ground prepolymer or a pearl polymer.

19. Dental material according to claim 1, comprising
- (a) 0.01 to 10 wt.-% hydroperoxide of Formula (I),
- (b) 0.001 to 5.0 wt.-% thiourea and/or thiourea derivative,
- (c) 5 to 95 wt.-% radically polymerizable monomer,
- (d) 0 to 85 wt.-% filler, and
- (e) 0.01 to 5 wt.-% additive,
in each case relative to the total mass of the material.

20. Dental material according to one of the preceding claims, which contains
- (a) 0.05 to 8.0 wt.-% hydroperoxide of Formula (I),
- (b) 0.003 to 4.0 wt.-% thiourea and/or thiourea derivative,
- (c) 10 to 95 wt.-% radically polymerizable monomer,
- (d) 0 to 85 wt.-% filler, and
- (e) 0.1 to 3 wt.-% additive,
in each case relative to the total mass of the material.

21. Dental material according to one of the preceding claims, which contains
   (a) 0.1 to 3.0 wt.-% hydroperoxide of Formula (I),
   (b) 0.005 to 3.0 wt.-% thiourea and/or thiourea derivative,
   (c) 10 to 90 wt.-% radically polymerizable monomer,
   (d) 0 to 85 wt.-% filler, and
   (e) 0.1 to 2 wt.-% additive,
   in each case relative to the total mass of the material.

22. Dental material according to claim 19, which comprises 50 to 85 wt.-% or 10 to 70 wt.-% filler.

23. Dental material according to claim 1 for therapeutic application, as dental cement, filling composite or veneering material.

24. Non-therapeutic use of a dental material according to claim 1, for the production or repair of dental restorations, prostheses, artificial teeth, inlays, onlays, crowns, bridges and complete dentures.

\* \* \* \* \*